US00PP20028P3

(12) United States Plant Patent
Zeppa

(10) Patent No.: US PP20,028 P3
(45) Date of Patent: May 26, 2009

(54) APPLE TREE NAMED 'RS103-130'

(50) Latin Name: *Malus domestica*
Varietal Denomination: RS103-130

(75) Inventor: Aldo Zeppa, Brisbane (AU)

(73) Assignee: State of Queensland Through Its Department of Primary Industry and Fisheries, Brisbane, Queensland (AU)

( * ) Notice: Subject to any disclaimer, the term of this patent is extended or adjusted under 35 U.S.C. 154(b) by 0 days.

(21) Appl. No.: 11/728,621

(22) Filed: Mar. 26, 2007

(65) Prior Publication Data

US 2008/0244795 P1 Oct. 2, 2008

(51) Int. Cl.
*A01H 5/00* (2006.01)

(52) U.S. Cl. ..... Plt./161

(58) Field of Classification Search ..... Plt./161
See application file for complete search history.

*Primary Examiner*—Annette H Para
*Assistant Examiner*—Louanne C Krawczewicz Myers
(74) *Attorney, Agent, or Firm*—Davis Wright Tremaine LLP

(57) ABSTRACT

A new and distinct apple tree variety, *Malus domestica* cv. 'RS103-130' is characterized by a compact medium sized tree with variegated leaf colour yielding red-skinned. fruit. The new variety is further characterized as resistant to apple scab (Races 1 to 5) incited by the fungus *Venturia inaequalis*.

7 Drawing Sheets

Latin name of the genus and species of the plant claimed: *Malus domestica.*
Variety denomination: 'RS103-130'.

BACKGROUND AND SUMMARY OF THE INVENTION

This invention relates to the discovery and asexual propagation of a new and distinct variety of apple tree, *Malus domestica* cv. 'RS103-130', as herein described and illustrated. The new variety 'RS103-130' was first hybridized by controlled pollination. The new variety 'RS103-130' is a compact medium sized tree with variegated leaf colour yielding red-skinned fruit. The tree and the fruit of new variety 'RS103-130' are resistant to apple scab (Races 1 to 5) incited by the fungus *Venturia inaequalis.*

The seed parent is 'Royal Gala' (the subject of U.S. Patent Pat. No. 4,121) and the pollen parent is 'CPR7T90' (unpatented, a scab resistant selection from a co-operative breeding program). The new variety 'RS103-130' was selected and evaluated at the fruiting stage at a research station located at Queensland, Australia. The new apple tree variety 'RS103-130' was first asexually propagated by grafting and budding onto seedling rootstocks in 1996 at the research station at Queensland, Australia, namely by grafting via top-working mature trees on MM.106 rootstock and budding via bench-grafting onto MM.106 rootstock and planting in a nursery bed for tree production.

The new apple tree cultivar, 'RIS103-130', is quite distinct from its seed parent, 'Royal Gala', and may be distinguished in the following characteristics: The new apple tree cultivar matures approximately 5 weeks later than the seed parent 'Royal Gala', that is the new apple tree cultivar matures in mid-March while the seed parent 'Royal Gala' matures in early February.

The new apple tree cultivar, 'RS103-130', can be distinguished from its pollen parent in the following characteristics: 'CPR7T90' is a breeding line that matures approximately three weeks after 'RS103-130'. At the research station at Queensland, Australia, 'CPR7T90' is a solid red (RHS 46A) block colour, without apparent stripes.

The new apple tree cultivar 'RS103-130' may be distinguished from presently available cultivars, for example, from 'Red Braeburn' and 'Fuji', by the following distinguishing characteristics: the tree and fruit of the new apple cultivar is more disease resistant than 'Red Braeburn' and 'Fuji'. 'Red Braeburn' and 'Fuji' are apple scab susceptible while the new apple tree cultivar is resistant to black spot (races 1 to 5) incited by the fungus *Venturia inaequalis.*

The new apple tree variety cv. 'RS103-130' has been shown to maintain its distinguishing characteristics through successive asexual propagations by, for example, budding onto seedling rootstocks.

BRIEF DESCRIPTION OF THE DRAWINGS

The accompanying photographic illustrations show typical specimens in full colour of the foliage and fruit of the new apple tree variety cv. 'RS103-130'. The colours are as nearly true as is reasonably possible in a colour representation of this type.

DETAILED DESCRIPTION OF THE PREFERRED EMBODIMENT

Figure 1:
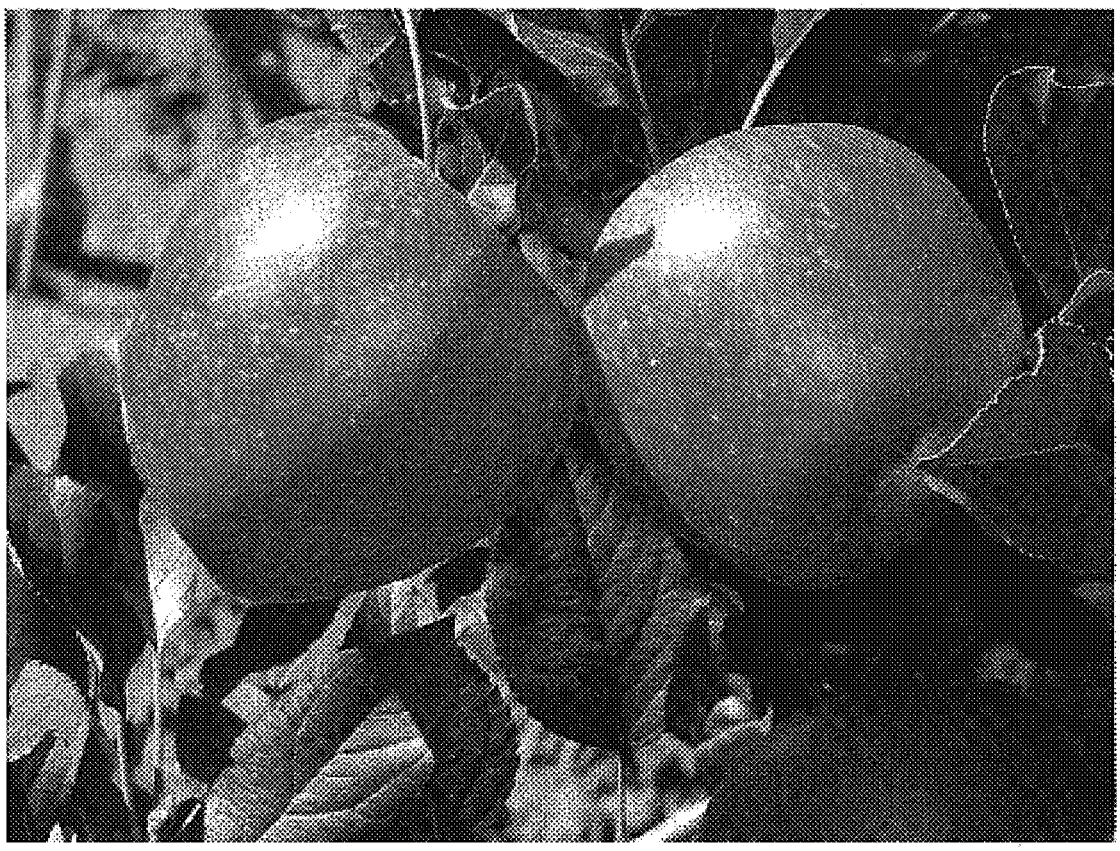
FIG. 1 is a photograph of the fruit of the new apple variety cv. 'RS103-130'.
Figure 2:
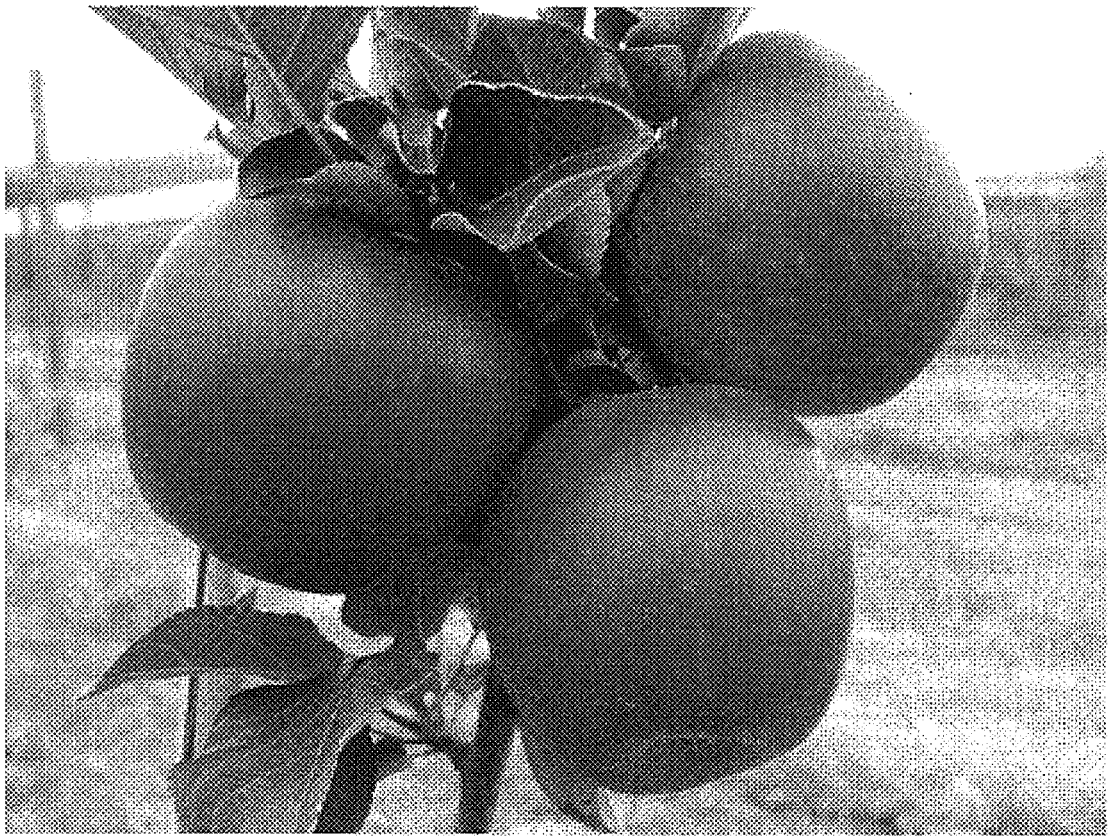
FIG. 2 is a photograph of the coloured side of fruit of the new apple variety cv. 'RS103-130'.
Figure 3:
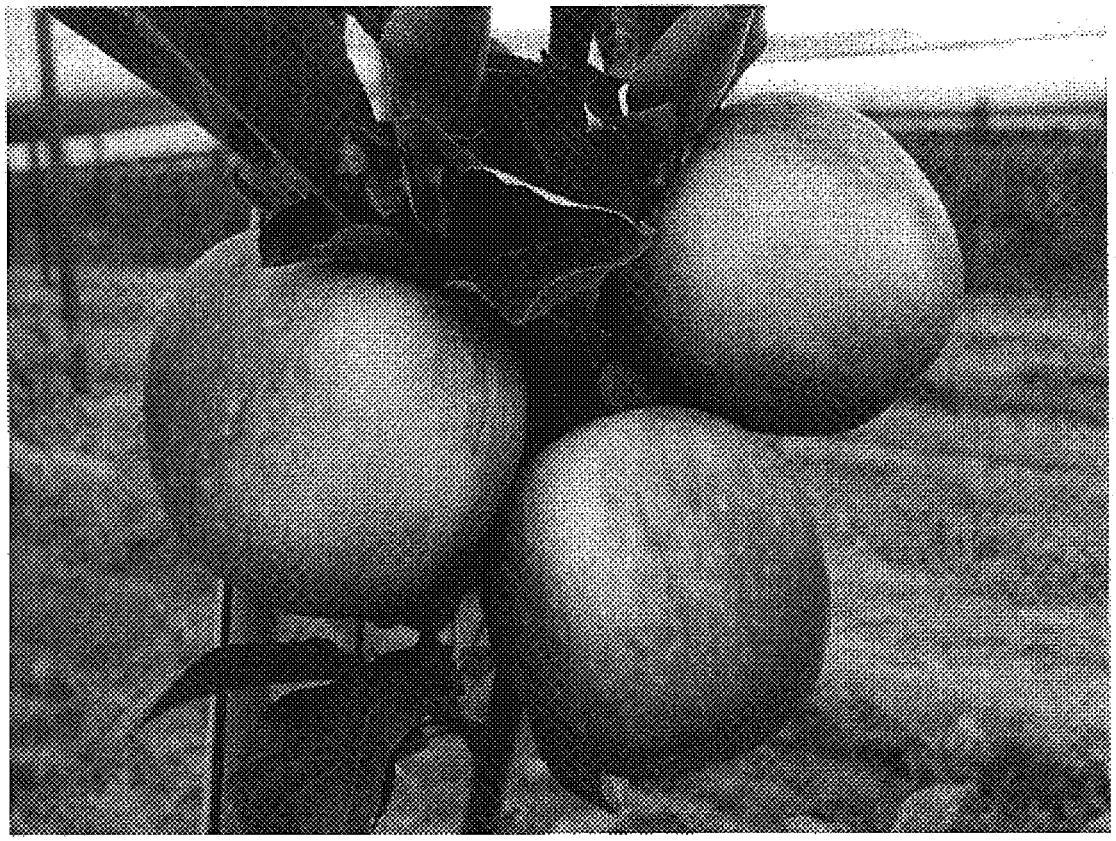
FIG. 3 is a photograph of the reverse side of the fruit of the new apple variety cv. 'RS103-130'.
Figure 4:
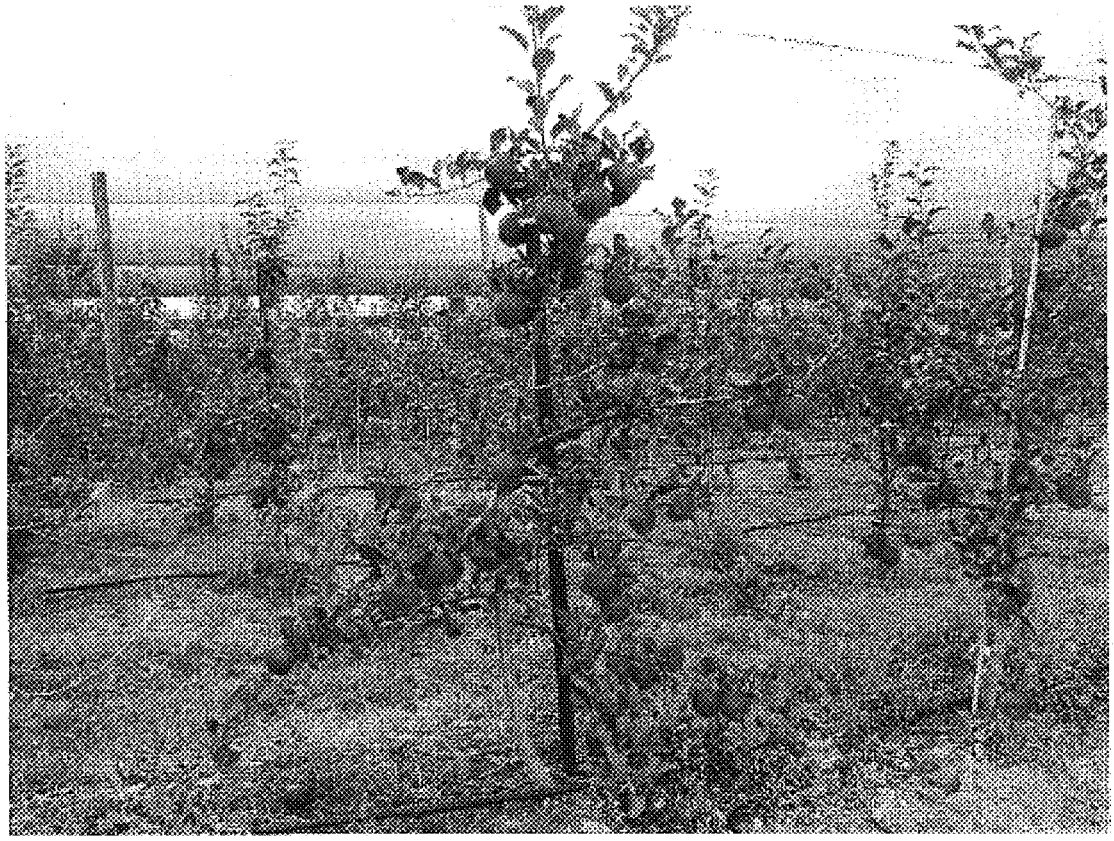
FIG. 4 is a photograph of fruit of the new apple variety cv. 'RS103-130' on the tree (coloured side).
Figure 5:
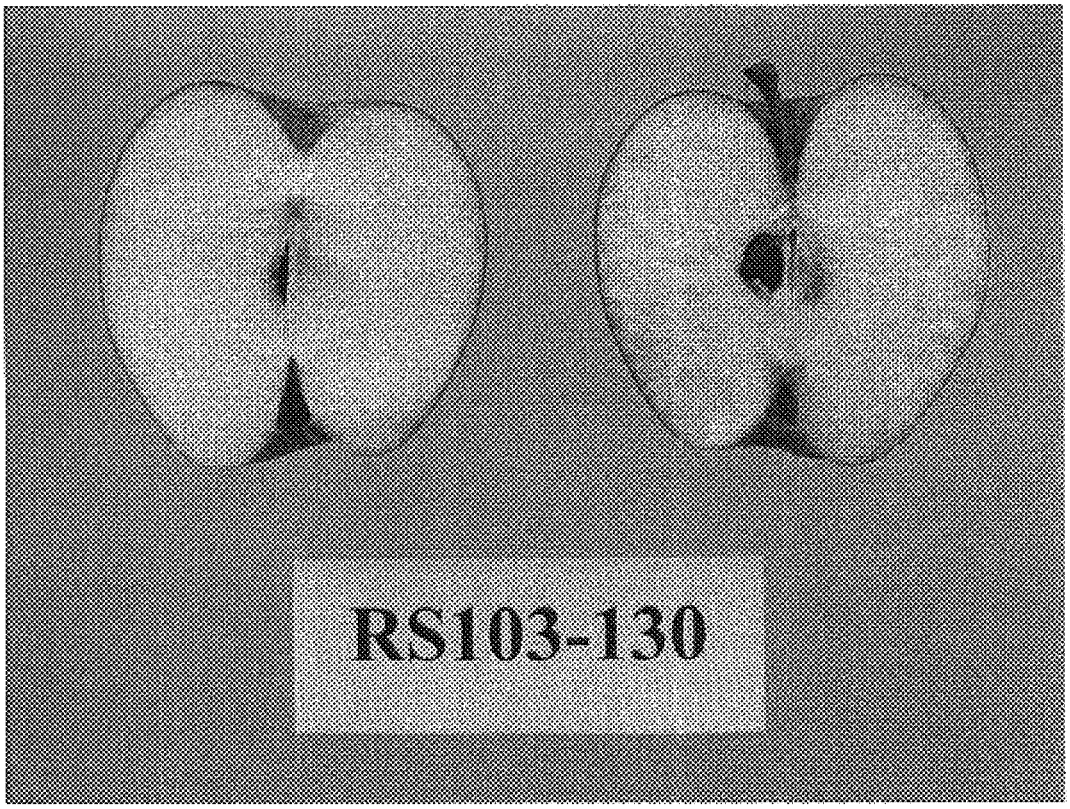
FIG. 5 is a photograph of the fruit of the new apple variety cv. 'RS103-130' cut in half to view the inside flesh of the fruit.
Figure 6:
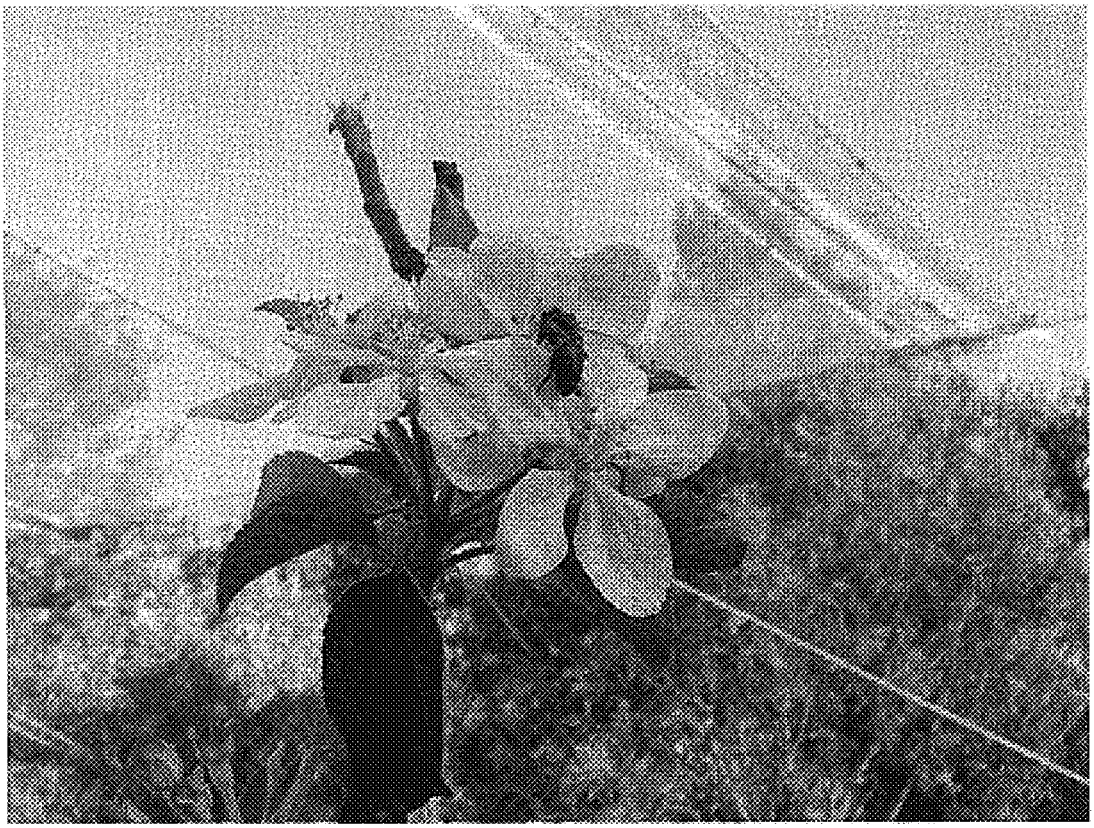
FIG. 6 is a photograph illustrating the flowers of the new apple variety cv. 'RS103-130'.
Figure 7:
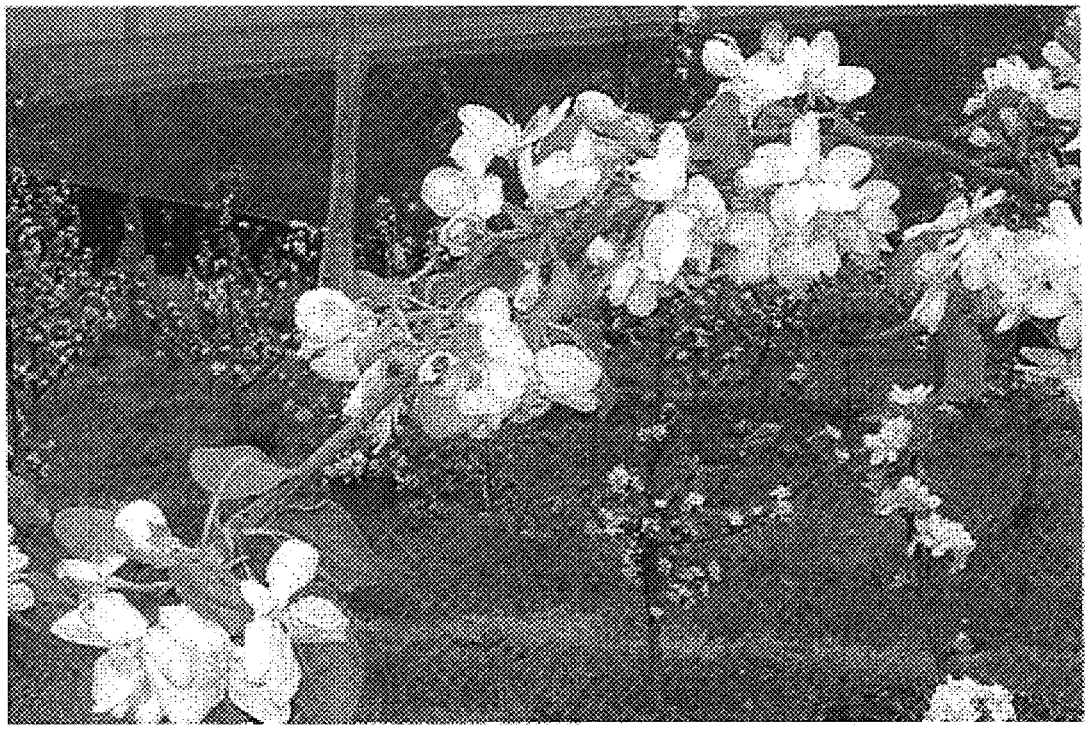
FIG. 7 is a photograph illustrating the flowers of the new apple variety cv. 'RS103-130'.

Throughout this specification, colour names beginning with a small letter signify that the name of that colour, as used in common speech, is aptly descriptive. Colour names beginning with a capital letter designate values based upon the R.H.S. Colour Chart published by The Royal Horticultural Society, London, England.

The descriptive matter which follows pertains to 'RS103-130' apple trees as well as to the comparative varieties 'Royal Gala' (the subject of U.S. Pat. No. 4,121), 'CPR7T90' (unpatented), 'Red Braeburn' (unpatented) and 'Fuji' (unpatented), grown at a research station located at Queensland, Australia.

Conventional cross pollination was undertaken in 1993 as per the methods described by Janick & Moore (Eds.) in *Methods in Fruit Breeding* with controlled pollination between 'Royal Gala' (seed parent) and 'CPR7T90' (pollen parent). The fruit produced by the procedure were allowed to develop until mature, followed by harvest of the fruit and extraction of the seeds. The seeds were vernalised for a period of up to twelve weeks (moist and at 2° C.) until ready for germination. This produced a family of apple seedlings which were inoculated at the 3 to 5 leaf stage with a fungal suspension of apple eonidia ($2.5\times10^5$ spores/mL) in order to cull susceptible seedlings. Resistant seedlings were field planted in July 1995 at the research station at Queensland, Australia, and 'RS103-130' selected in 1999 for fruit quality parameters of a striped red to block red colour, sweetness, crispness and low acidity.

In 1996, scion wood was vegetatively propagated by top-working onto mature 'Royal Gala' trees on MM106 stock while concurrently bench-grafted to MM106 stock for nursery tree production. In subsequent years scion wood from the trees propagated in 1996 had been used to establish two major trial plantings:

(1) a fruit production block (620 Trees) at the research station at Queensland, Australia, and (2) an organic apple production block on the property of a Stanthorpe apple grower (1 & L Rizzato & Sons, Queensland, Australia, 625 trees).

Fruiting at these two trial sites has shown no evidence of off-types after two generations of vegetative propagation. Further to this, a budwood multiplication block (12 trees) on seedling and MM106 rootstocks had also been established at the research station at Queensland, Australia with no evidence of off-types.

Asexual reproduction of this new variety by grafting and budding onto rootstock shows that the foregoing and all other characteristics and distinctions come true to form and are established and transmitted through succeeding propagations. The fruit of the subject were grown on M.26 rootstocks in a 10 by 6 m complete randomized block design orchard planting, at the research station at Queensland, Australia. This block has been planted for the purposes of obtaining data for Plant Breeders' Rights under Australian legislation.

Pest and disease treatments were applied as required. Irrigation and fertilizer application followed commercial practice. 10 to 20 random measurements of each characteristic were obtained from each replicate.

Certain characteristics of this variety, such as growth and colour, may change with changing environmental conditions (e.g., light, temperature, moisture), nutrient availability, rootstocks, or other factors. Colour descriptions and other terminology are used in accordance with their ordinary dictionary descriptions, unless the context clearly indicates otherwise. Colour names beginning with a capital letter designate values based upon The R.H.S. Colour Chart published by the Royal Horticultural Society, London, England.

The following information has been determined from the averages of data measured from a sampling of the trees of 'RS 103-130' grown in the Plant Breeder's Right block, at the research station at Queensland, Australia. The observations described herein are believed to apply to plants of the variety 'RS103-130' grown under similar conditions of soil and climate elsewhere.

TREE

General: Measurements were taken on trees that were 3 years of age growing on M.26 rootstock in Queensland, Australia. Numbers provided are averages of data measured from the sampling of trees.

*Vigor.*—Low to moderate.

*Overall shape.*—Spreading to slight drooping.

*Height.*—Approximately 2.02 m.

*Width.*—Approximately 1.38 m.

*Caliper.*—Approximately 32 mm at 100 mm above the graft union, and ranging from approximately 100 mm to approximately 300 mm above the ground.

*Trunk.*—Medium Stocky.

*Trunk bark texture.*—Smooth with raised, prominent lenticels.

*Trunk bark colour.*—About Greyed-Green colour RHS 197D.

*Patches or other markings.*—No prominent spots or scales evident.

*Primary branches.*—Stout; Branches emerge at an angle of approximately 60 to approximately 90 degrees with branches higher in the tree emerging at approximately 60 degrees. Exemplary 2-year-old primary branches have been observed to have a caliper of approximately 12.2 mm measured at the base. Measured trees are grown to a central leader system. The typical and observed lateral branch length is 116.3 cm (first primary branch above graft union and arising from main stem). The diameter of the stem/trunk of the tree measured by calliper at 300 mm above the crotch was an average of 28.9 mm (the crotch on a central leader tree being identified as the point where the first lateral limb emerges).

*Branch colour.*—One-year old branches are about Brown RHS 200D in colour, while older branches are about Grey-Brown RHS 199C in colour.

*Branch pubescence.*—Absent.

*Branch lenticels.*—Low to medium density, approximately 5 per square centimeter; Shape: Oval Colour: About Greyed-White RHS 156D. Size: Approximately 1.2 mm long by approximately 0.9 mm wide.

*Internodes.*—Average internode length is approximately 2.0 cm for a 1-year old shoot.

*Bearing.*—Annual.

*Hardiness.*—Australian Zone hardy, comparable to 'Cripps Pink'.

*Drought and insect resistance.*—Comparable to 'Cripps Pink'.

*Disease resistance.*—Bred using parent with Vf gene complex conferring resistance to apple scab incited by the fungus *Venturia inaequalis*.

LEAVES

*Texture.*—Leathery.

*Sheen.*—Medium Glossy to slightly dull.

*Length.*—Approximately 4.9 cm to approximately 11.0 cm; average approximately 8.4 cm (average measurement from 50 typical leaves).

*Width.*—Approximately 3.7 cm to approximately 7.1 cm, average approximately 4.9 cm (average measurement from 50 typical leaves).

*Petiole.*—Length: Approximately 35.0 mm. Diameter: Approximately 1.4 mm. Colour: About Green RHS 138B, tinged with about Greyed-Purple RHS 185B at point of attachment.

*Margin.*—Finely serrated.

*Tip surface.*—Acute.

*Stipules.*—Either 1 or 2 present on only 25% of leaves. Where present, opposite, slender (approximately 0.14 mm to approximately 0.95 mm), colour about Yellow-Green RHS 147C, length approximately 3.3 mm to approximately 15.9 mm.

*Leaf colour.*—Upper leaf surface: About Yellow-Green RHS 147 A Lower leaf surface: About Yellow-Green RHS 147C.

*Leaf vein colour.*—From about Greyed-Purple RHS 185B at the base of the leaf (point of attachment to petiole) to about Green-White RHS 157B at the apex.

*Pubescene.*—Absent to very fine on upper surface, to fine (light) on lower surface.

FLOWERS

General:

*Size.*—Medium. Approximately 37.7 mm in diameter fully flattened.

*Shape.*—Ovoid to round.

*Colour.*—Unopened bud: King Bloom Length: Approximately 12.5 mm to approximately 16.2 mm (average approximately 14.46 mm); Diameter: Approximately 9.7 mm to approximately 11.9 mm (average approximately 10.74 mm) Color: About Red-Purple RHS 63C. Opened bud: Color: About White RHS 155D with streaks to about Red-Purple RHS 62D. Flower: Upper petal surface: About White RHS 155D to about Red-Purple RHS 62D. Lower petal surface: About White RHS 155D to about Red-Purple RHS 62B.

Petals:

*Numbers of petals per flower.*—5.

*Petal size.*—Length: Approximately 17.72 mm. Width: Approximately 12.05 mm.

*Petal shape.*—Ovate in shape. Base: Slightly acuminate. Apex: Rounded.

*Arrangement.*—Their arrangement is separated but over-lapping.

Sepals:

*Number.*—About 5 per flower.

*Length.*—Approximately 6.34 mm.

*Width.*—Approximately 4.30 mm wide.

*Color.*—About Green RHS 143D, tinged at the tip with about Red-Purple RHS 59A.

*Arrangement.*—Arranged separately.

Pedicel/Peduncle: Apples do not have branched inflorescences hence no pedicels. The flower stalk of an apple is the peduncle.

*Length.*—Approximately 10.44 mm (measured to where receptacle is swelling).

*Diameter.*—Approximately 1.06 mm.

*Colour.*—About Yellow-Green RHS 145C.

Stamen:

*Number.*—Approximately 20 per flower, arranged in a row around the circumference of the receptacle.

*Length.*—Approximately 3.65 to approximately 11.67 mm.

*Filament color.*—About White RHS 155C.

*Anthers.*—About 20 per flower. Anther Color: About Yellow RHS SD Unopened Anther Color: About Yellow RHS 5D.

*Pollen color.*—About Yellow RHS 4B.

Pistil:

*General.*—The stigma is about approximately 1 mm long; styles are 5 in number, separated at base but held tightly and entangled by fine hairs, and about Yellow-Green RHS 144B in colour.

Pollination Requirements: An early flowering variety e.g. 'Braeburn' is preferred. Later flowering varieties e.g. 'Granny Smith' or 'Cripps Pink' will overlap sufficiently in flowering to enable pollination.

Fragrance: Slight.

Bloom season: In 2006 at the research station in Queensland, Australia, blooming began on the 18$^{th}$ of September with full bloom on the 28$^{th}$ of September finishing on the 3$^{rd}$ of October.

FRUIT

General: Measurements are the average of 10 typical 'RS103-130' apples.

Size: Medium to large.

*Length.*—Approximately 71.3 mm.

*Width.*—Approximately 81.4 mm.

Shape: Asymmetrical, conic; slight ribbing is present; very slight lobes observed at calyx end. The calyx ranges from slightly open to open (1.9 mm to 6.9 mm — with an average of 3.9 mm for ten fruit).

*Cavity.*—Approximately 38.6 mm wide with a depth of approximately 20.6 mm.

*Basin.*—Concave shaped and approximately 28.4 mm wide with a depth of approximately 8.0 mm.

Fruit stem:

*Length.*—Approximately 10.5 mm.

*Diameter.*—Approximately 2.8 mm.

*Color.*—About Yellow-Green RHS 144B.

Locules: 5 slightly open locules with seeds free of the carpel wall at maturity. Locule length approximately 16.6 mm (average of ten fruit cut longitudinally). Locule width approximately 9.9 mm (average of 50 locules from ten fruit with transverse cut).

Fruit Skin:

*Tendency to crack.*—Absent.

*Thickness.*—Medium.

*Surface texture.*—Glossy with a tendency to become greasy at maturity.

*Lenticels.*—Are present, approximately 0.5 to approximately. 1.0 mm in diameter, generally cream in colour (RHS yellow-white 158A), and at an average density of about 4 lenticels /cm$^2$.

*Colour.*—General colour effect: About Red RHS 53A. Ground colour:. At maturity, about Yellow-Green RHS 154C. Over colour: About Red RHS 53A with paler sections about Red RHS 53B. Russetting: Slight amount inside stem cavity.

Flesh:

*Flavor.*—Mild, sweet, low-acid flavour.

*Brix.*—Approximately 14.1 to approximately 18.1 Brix (Average approximately 15.7 Brix).

*Juiciness.*—Moderately juicy.

*Colour.*—About Yellow RHS 8C.

*Aroma.*—Slight.

Core: While the calyx can be open in about 70 percent of fruit, the calyx tube is closed and the core lines are defined.

*Shape.*—Round to slightly elongate.

*Diameter.*—Approximately 32.1 mm.

*Number of bundles.*—Approximately 10 per fruit.

*Core length.*—Approximately 46.1 mm (measured from point of fruit stem attachment to calyx end at point of sepal attachment).

*Calyx tube length.*—Approximately 16.2 mm (measured as length from the calyx end at point of sepal attachment to the point of calyx tube closure).

Seed:

*Number.*—About 1 to 2 seeds per cell.

*Shape.*—Acute in shape.

*Length.*—Approximately 8.7 mm.

*Width.*—Approximately 5.6 mm wide.

*Color.*—About Greyed-Orange RHS 165A.

Fruit production: First picking date in the 2006 season at the research station at Queensland, Australia, was about the 20$^{th}$ of March, and last picking date was about 29$^{th}$ of March.

Storage: Fruit remains fresh at room temperature (approximately 20° C.) for approximately 7 days, and can be stored up to approximately 4 months in cold storage (about 1° C. or about 34° F.).

Usage: Fresh eating. Ten typical apples of 'RS103-130' and of the cultivar 'Braeburn' from trees growing near to one another, were obtained on the 5$^{th}$ of April 2006 and tested for certain properties. The approximate averages of these properties were as follows:

TABLE 1

COMPARISON OF 'RS103-130' WITH OTHER APPLE VARIETIES

| | 'RS103-130' | 'Braeburn' |
|---|---|---|
| Firmness (pressure kg/cm$^2$) | 9.2 | 7.2 |
| Starch Index On Scale of 1 (high starch) to 6 (low starch) | 5.5 | 5.5 |
| Soluble Solids (in percent) | 15.7 | 12.7 |
| Apple scab resistance (Scab resistant/scab susceptible) | Scab Resistant | Scab susceptible |

What is claimed is:

1. A new and distinct apple tree as herein described and illustrated.

* * * * *